United States Patent [19]

Edwards et al.

[11] Patent Number: 5,429,242

[45] Date of Patent: * Jul. 4, 1995

[54] LAMINATED BAGS FOR CONTAINERIZATION OF TOXIC OR HAZARDOUS MATERIALS

[75] Inventors: David B. Edwards; William J. McCarthy, both of Ongar, England; Leonard E. Hodakowski, Raleigh, N.C.; Chi-Yu R. Chen, Raleigh, N.C.; Samuel T. Gouge, Raleigh, N.C.; Paul J. Weber, Durham, N.C.

[73] Assignee: Rhone-Poulenc Agriculture Ltd., Ongar, England

[ * ] Notice: The portion of the term of this patent subsequent to Jan. 25, 2011 has been disclaimed.

[21] Appl. No.: 147,602

[22] Filed: Nov. 4, 1993

Related U.S. Application Data

[63] Continuation of Ser. No. 41,521, Mar. 31, 1993, Pat. No. 5,280,835, which is a continuation-in-part of Ser. No. 680,321, Apr. 4, 1991, abandoned, which is a continuation-in-part of Ser. No. 679,290, Apr. 2, 1991, abandoned, and Ser. No. 554,615, Jul. 18, 1990, Pat. No. 5,080,226.

[51] Int. Cl.6 .................................................. B65D 65/40
[52] U.S. Cl. .................................. 206/484; 206/524.7
[58] Field of Search ............... 206/0.5, 204, 205, 219, 206/524.1, 524.2, 524.6, 524.7, 525, 568, 484; 71/DIG. 1; 252/315.1; 424/409, 412; 514/801, 812

[56] References Cited

U.S. PATENT DOCUMENTS

| | | |
|---|---|---|
| 4,765,916 | 8/1988 | Ogar et al. . |
| 4,846,992 | 7/1989 | Fonsny ............................ 206/524.7 |
| 5,280,835 | 1/1994 | Edwards et al. ................. 206/524.7 |

FOREIGN PATENT DOCUMENTS

| | | |
|---|---|---|
| 0234867 | 9/1987 | European Pat. Off. ......... 206/524.7 |
| 0457600 | 11/1991 | European Pat. Off. ......... 206/524.7 |
| 1824283 | 1/1960 | Germany . |
| 1862386 | 7/1962 | Germany . |
| 3017246 | 6/1980 | Germany . |
| 55/4336 | 1/1980 | Japan . |
| 2108534 | 4/1990 | Japan ............................. 206/524.7 |
| 0922317 | 3/1963 | United Kingdom ............ 206/524.7 |
| 89/04282 | 5/1989 | WIPO . |
| 89/12590 | 12/1989 | WIPO . |
| 8912587 | 12/1989 | WIPO ............................. 206/524.7 |

Primary Examiner—Jimmy G. Foster

[57] ABSTRACT

A package which comprises a hazardous chemical dissolved or dispersed in a liquid or gel contained in a water soluble or water dispersible laminated film. The laminated film construction provides improved resistance to puncture or breakage thereby providing an improved containerization system for toxic or hazardous products.

22 Claims, No Drawings

LAMINATED BAGS FOR CONTAINERIZATION OF TOXIC OR HAZARDOUS MATERIALS

This a continuation of application Ser. No. 08/041,521 filed Mar. 31, 1993, U.S. Pat. No. 5,280,835, which is is a continuation-in-part of a U.S. patent application Ser. No. 07/680,321, filed Apr. 4, 1991, abandoned, which is a continuation-in-part of U.S. patent application Ser. No. 07/679,290, filed Apr. 2, 1991, abandoned, and U.S. patent application Ser. No. 07/554,615, filed Jul. 18, 1990, U.S. Pat. No. 5,080,226, all of which are incorporated herein by reference.

BACKGROUND OF THE INVENTION

I. Field of the Invention

This invention relates to a package comprising a liquid chemical or chemical dissolved or dispersed in a liquid or gel which is contained in an envelope of water soluble or water dispersible material.

II. Discussion of the Prior Art

At present, most hazardous liquids are stored in metal drums or, where smaller quantities are required, plastic containers.

Hazardous compounds, especially agrochemical compounds, are formulated in a variety of ways. It is, however, especially desirable for farmers to handle such compounds when they are in liquid form. This facilitates the spreading of such compounds. There are, however, difficulties and drawbacks in handling liquids. The liquids can be spilled on the ground or may leak due to holes in the containers. The containers may also rupture when subjected to a physical shock.

It is thus difficult to devise a containerization system that is suitable for farmers, safe for those handling the containers and also safe for the environment.

It is known that agrochemicals may be contained in soluble bags or sachets made from film. However, such films may crack and break and thus cause spillage of the agrochemicals they contain. In fact, a variety of defects may be present in films, which lead to weaknesses of the film and consequently a potential source of leakage. The presence of air bubbles, dust particles or other foreign bodies, of gel particles or of thin points on or in the film are all potential weak points. If a film with such a weak point is subjected to a lot of handling or physical shock, the film may fail at that point. This is especially a problem in the agrochemical industry where containers may be subjected to rough or unsafe handling by distributors or farmers.

The weaknesses of films mentioned above are present to a greater or lesser extent in certain types of films, depending on their method of manufacture. When films are made by casting, there may be fewer pinholes, but there are more often tiny pieces of gel inclusions. When films are made by extrusion, there are more pinholes.

SUMMARY OF THE INVENTION

The present invention seeks to provide a new containerization system for agrochemicals which is safe to handle.

The invention further seeks to provide a new containerization system for agrochemicals which is convenient for endusers, e.g. farmers, to handle.

The invention further seeks to provide a new containerization system for agrochemicals which reduces the risks of pollution and environmental damage.

In one aspect, the invention seeks to avoid leakage of liquid or dissolved chemicals through the pinholes of a film containerization system. Although pinholes are generally rare, even the presence of one pinhole in many thousands of containers is enough to cause damage, since the liquid in the container passes through the pinhole and contaminates the surrounding environment.

Other objects and advantages of the invention will be apparent from the description which follows.

DETAILED DESCRIPTION OF THE PRESENT INVENTION

The containerization system of the invention is characterized in that a hazardous material in a liquid or gel form is contained in a water soluble or water dispersible bag made of a laminated film.

According to a preferred feature of the invention the hazardous compounds are agrochemicals, e.g. pesticides or plant protection agents or plant growth regulators.

The present invention accordingly provides a package which comprises a hazardous chemical dissolved or dispersed in a liquid or gel contained in a water soluble or water dispersible laminated film.

In this specification the term laminated film means a film which has been made from two or more originally separated layers which are joined together. The two layers may be joined together in the laminate by known methods. For example, the layers of the laminate may be joined by pressure, heating, crosslinking, fusion, adhesion or any combination thereof. Adhesion of the two layers may be obtained through the use of a separate adhesive, or, when appropriate, water.

When suitable water soluble or water dispersible layers are used, a particularly convenient way to obtain a laminated film is by adhesion of the separate layers, either using adhesive PVA (generally of low molecular weight) and/or more simply by means of water.

Because two or more layers are used to produce the laminated film, the chance of pinholes occurring in the film is reduced to almost nil. This is because it is unlikely that two pinholes in separate layers will overlap. Furthermore, the tensile strength of a multi (e.g. two) layer film is better than the tensile strength of a similar film of the same thickness that is made of a single layer.

The laminated films used in the invention generally have a thickness of from 10 to 250 microns, preferably from 15 to 80 microns. The individual layers constituting the laminated films which are used in the invention are generally each half of this thickness. When two layers are used, the ratio of thickness of the two layers is generally from 0.1 to 10, preferably from 0.5 to 2. Bags or sachets made of laminated films according to the invention generally have a content of from 0.2 to 12 liters, preferably from 0.45 to 6 liters.

The materials that may be used in the invention are water soluble or water dispersible materials which are insoluble in organic solvents used to dissolve or disperse the chemicals they are used to contain. Suitable materials include polyethylene oxide or methyl cellulose, but preferably the material comprises or is derived from polyvinylalcohol, i.e. partially or fully alcoholysed or hydrolysed, e.g., 40–99%, preferably 70–92% alcoholysed or hydrolysed polyvinyl acetate films.

The layers of the laminated films of the invention may be made of the same material or of different materials. Films made from layers of different materials may have advantageous properties. For example, an inner layer of a package may be made more resistant to the agrochemical it contains. In addition, the outer layer of the bag can be selected to have one or more of the following properties:
  i. to dissolve more quickly (compared to an inner layer or a single layer package) in water,
  ii. to have improved mechanical properties including improved resistance to mechanical damage,
  iii. to have improved machinability,
  iv. to have less susceptibility to relative humidity,
  v. to have resistance to freezing and/or high temperatures.

One of more of the layers of the laminated film may contain a plasticiser. A suitable plasticiser content in the inner layer may improve the sealing properties of the film, and make the film less likely to stretch. The film will thus be easier to process on machinery and to seal around the hazardous liquid. A suitable plasticiser content in the outside layer of the container makes the outer surface more flexible and thus more resistant to physical damage from low temperature or shock and movement.

The layers of the laminated film may be made using different techniques, e.g., extrusion or casting. A laminate made from layers produced by different methods may have advantageous properties including greater flexibility, increased strength and increased resistance to stretching. The increased strength and/or resistance to stretching may be in one direction in the film. The laminated films for use in the present invention are used to produce packages which avoid the time-consuming and hazardous consequences of prior art packages which leak in the filling process or during subsequent handling due to film defects.

As already said, the bags (or containerization system) may contain either liquids or gels. A preferred feature of the invention is the bags or containerization system of the invention containing a gel.

According to a particular feature of the invention, the gels are chosen in such a way that one or more of the following features are present:
  the resulting gels form a continuous system and/or
  the resulting gels have a viscosity of 500 to 50,000 centipoise, more preferably of 1000 to 12000 centipoise (these viscosities are Brookfield viscosities measured with a viscosimeter in form of a flat plate rotating at 20 round per minute)
  the gel has a phase difference phi between the controlled shear stress and the resulting shear strain such that tg(phi) is less than or equal to 1.5, preferably less than or equal to 1.2. Tg(phi) is the tangent of the angle phi (or phase difference). The measurement of phi is made by means of a rheometer having a flat fixed plate and a rotating cone above this plate such that the angle between them is less than 10 preferably less than 4°. The cone is caused to rotate by means of a controlled speed motor; the rotation is a sinusoidal one, i.e., the torque and the angular displacement change as a sine function with time. This angular displacement corresponds to the hereabove mentioned shear strain; the torque of the controlled speed motor (which causes the angular displacement) corresponds to the hereabove mentioned controlled shear stress.
  the gels preferably have a density greater than 1 gm/cc, preferably greater than 1.1 gm/cc.
  the gels have a spontaneity (as hereafter defined) less than 75, preferably less than 25.

The spontaneity is assessed according to the following method: A mixture of 1 ml gel with 99 ml water are put into a 150 ml glass tube which is stoppered and inverted through 180° (upside down). The number of times required to completely disperse the gel is called the spontaneity.

By the wording continuous system, it is meant a material which is visually homogeneous, that is to say which has the visual appearance of having only one physical phase; this does not exclude the possibility of having small solid particles therein, provided these particles are small enough not to constitute a visible separate physical phase.

It is known that a gel is generally a colloid in which the dispersed phase has combined with the continuous phase to produce a viscous, jelly-like product; it is also a dispersed system consisting typically of a high molecular weight compound or aggregate of small particles in very close association with a liquid.

In order to make a bag, the film needs to be shaped (possibly partially sealed) and then filled with the gel. Generally the gels are able to flow, even if it is a slow rate due to the high viscosity. A container which is used to contain the gels cannot be easily emptied due to this high gel viscosity (that is a reason why the gels have not been used up to now in agriculture). When filled, the bag must be finally sealed, generally heat sealed, to be closed.

According to another feature, the bag of the invention is filled to at least 60% of capacity with the agrochemical composition-containing substance, more preferably at least 70% of capacity, still more preferably 80 to 99% of capacity and most preferably 85 to 95% of capacity. The bag is preferably not filled to complete capacity because the unused capacity gives the bag shock resistance, i.e., resistance to breakage when dropped, transported or stored. This unused capacity may or may not contain air or an inert gas. An absence of air or inert gas in the unused capacity further improves shock resistance. However, in deciding how much unused capacity, or absence of air or inert gas, to provide, the advantages of shock resistance must be balanced against the need, if any, for shock resistance and the cost of providing shock resistance. For example, if the bag is stored and/or transported in a shock absorbing container, then it may not be as helpful to provide this unused capacity.

Also, the capacity to which the bag is filled, and whether the unused capacity does or does not contain air or inert gas, is affected by whether it is desired to have the bag sink or float. Whether the bag sinks or floats will depend not only on the unused capacity, but also on the density of the bag contents.

Further information may be found in the following copending applications, the disclosures of which are incorporated herein by reference: application of Leonard E. Hodakowski, Chi-Yu R. Chen, Samuel T. Gouge and Paul J. Weber for "Gel Formulations for Use in Toxic or Hazardous Product Containerization Systems" filed Jun. 11, 1991; application of Samuel T. Gouge, Leonard E. Hodakowski, Paul J. Weber and Chi-Yu R. Chen for "Gel Formulations for Hazardous Products" filed Jun. 11, 1991; application of Leonard E. Hodakowski, Chi-Yu R. Chen, Samuel T. Gouge and Paul J. Weber for "Water Dispersible Gel Formulations" filed Jun. 11, 1991; application of Leonard E. Hodakowski, Ricky W. Couch, Samuel T. Gouge and Robert C. Ligon for "Gel Formulations" filed Jun. 11, 1991; and application of Samuel T. Gouge and James E. Shue for "Bag In A Bag For Containerization of Toxic or Hazardous Material" filed Jun. 11, 1991.

The following Examples are given by way of illustration and should not be understood to restrict the scope of the invention.

EXAMPLE 1

A film in a roll form is constructed from two thinner films by lamination: both films are made from a 88% hydrolysed polyvinyl alcohol (cold water soluble), each 25 microns thick; one has a 17% plasticiser content, the other has a 15% plasticiser content. The two films are laminated together with heat (100° C.) and pressure to form one film of 50 microns thickness.

The film is then used to produce 1 liter sachets containing a solvent based liquid herbicide (mixture of ioxynil and bromoxynil esters) by using "form-and-fill" methods. The herbicide is a solution in a C10 aromatic hydrocarbons mixture as solvent.

The film is placed on the machine so that the high plasticiser layer is produced on the outside of the sachets. The film is thus easy to process.

No leak is observed during the manufacture, handling, and transporting of 500 sachets.

EXAMPLE 2

A gel is made by stirring at 50° C. a mixture of:
Active ingredient: 2,4-D phenoxy benzoic acid isooctyl ester): 64.8%
Solvent: aromatic solvent with flash point of 65° C.: 24.2%

| Surfactant: a mixture of | |
|---|---|
| a non ionic/sulfonate blended emulsifier | 4% |
| and calcium alkylbenzene sulfonate | 1% |

Gelling agent: mixture of dioctylsulfosuccinate salt and sodium benzoate: 6%

The mixture is stirred and shaken until each component is dissolved or dispersed.

During stirring, a dissolution appears, and thereafter a gellation. Gellation is increased during the cooling at room temperature (20° C.).

The brookfield viscosity of the gel is 3000 centiposise.

The emulsion stability is good in the above described test.

1100 g of this gel are put in a 1 liter bag made of a film of PVA similar to the film of example 1. The bag, which is almost full (about 95% v/v), is heat sealed. The density both of the gel and of the bag containing the gel is 1.1.

The bag is then dropped 10 times from 1.2 m onto the ground. No breaking or leakage is observed.

Another bag made in the same way as the previous one is tested for pinhole protection. A needle (diameter: 0.6 mm) is passed through the bag. It is observed that a small droplet forms at the locus where the needle passed, but this droplet was small enough not to drop from the bag and not to flow along the bag.

What is claimed is:

1. A package which comprises a bag containing a hazardous chemical, said hazardous chemical being dissolved or dispersed in a liquid or gel, said bag being made of a film comprised of at least two laminated water soluble water dispersible layers; said laminated layers completely enclosing said hazardous chemical contained in said bag.

2. A package according to claim 1, wherein the hazardous chemical is dissolved or dispersed in a liquid.

3. The package according to claim 1, wherein the hazardous chemical is dissolved or dispersed in a gel.

4. The package according to any one of claims 1, 2 or 3, wherein the laminated film has a thickness of from 10 to 250 microns.

5. The package according to any one of claims 1, 2 or 3, which has a content of hazardous chemical of from 0.2 to 12 liters.

6. The package according to any one of claims 1, 2 or 3, wherein at least one of the layers of the film is selected from polyethylene oxide, methyl cellulose or partially or fully alcoholized or hydrolysed polyvinyl acetate.

7. The package according to any one of claims 1, 2 or 3, wherein at least two of the layers of the laminated film are made of the same material.

8. The package according to any one of claims 1, 2 or 3, wherein at least two of the layers of the laminated film are made of a different material.

9. The package according to any one of claims 1, 2 or 3, wherein the laminated film consists essentially of two layers.

10. The package according to any one of claims 1, 2 or 3, wherein the bag is made by laminating two or more layers together by pressure, heating, crosslinking, fusion or by means of water to obtain the laminated film.

11. The package which comprises a bag containing a hazardous chemical dissolved or dispersed in a liquid or gel, said bag being made of a film comprised of plural laminated water soluble or water dispersible layers, said plural laminated layers completely enclosing said hazardous chemical contained in said bag.

12. The package according to any one of claim 11, wherein the water soluble or water dispersible laminated film is insoluble in the liquid or gel used to dissolve or disperse the hazardous chemical.

13. The package according to claim 11, wherein at least one of the layers of the film is selected from polyethylene oxide, methyl cellulose or partially or fully alcoholized or hydrolysed polyvinyl acetate.

14. The package according to any one of claim 11, wherein the bag is made by laminating two or more layers together by pressure, heating, crosslinking, fusion or by means of water to obtain the laminated film.

15. The package which comprises a bag containing a hazardous chemical dissolved or dispersed in a gel, said bag being made of a film comprised of plural laminated water soluble or water dispersible layers, said plural laminated layers completely enclosing said hazardous chemical contained in said bag.

16. The package according to any one of claim 15, wherein the water soluble or water dispersible laminated film is insoluble in the gel used to dissolve or disperse the hazardous chemical.

17. The package according to any one of claim 15, wherein at least one of the layers of the film is selected from polyethylene oxide, methyl cellulose or partially or fully alcoholized or hydrolysed polyvinyl acetate.

18. The package according to anyone of claim 15, wherein at least two of the layers of the laminated film are made of the same material.

19. The package according to any one of claim 15, wherein at least two of the layers of the laminated film are made of a different material.

20. The package according to any one of claim 15, wherein the laminated film consists essentially of two layers.

21. The package according to any one of claim 15, wherein the bag is made by laminating two or more layers together by pressure, heating, crosslinking, fusion or by means of water to obtain the laminated film.

22. The package according to any one of claim 15, wherein the package is filled with the gel to at least 60% of capacity.

* * * * *